United States Patent [19]

Vazquez

[11] Patent Number: 4,893,477

[45] Date of Patent: Jan. 16, 1990

[54] FROZEN FOODSTUFFS THAWING DETECTOR DEVICE

[76] Inventor: Jose A. G. Vazquez, Pedroneras, 40, 28043 Madrid, Spain

[21] Appl. No.: 129,284

[22] Filed: Dec. 7, 1987

[30] Foreign Application Priority Data

Dec. 10, 1986 [ES] Spain .................................. 8603349

[51] Int. Cl.$^4$ .............................................. F25B 49/00
[52] U.S. Cl. ..................................... 62/125; 374/160; 426/88
[58] Field of Search ................... 62/125, 129, 130; 374/160; 116/217; 426/88

[56] References Cited

U.S. PATENT DOCUMENTS

| | | | |
|---|---|---|---|
| 1,535,536 | 4/1925 | MacDonald | 62/125 X |
| 1,917,048 | 7/1933 | Midgley, Jr. | 62/125 X |
| 2,216,127 | 10/1940 | McNaught | 62/125 X |
| 3,140,611 | 7/1964 | Kliewer | 62/129 X |
| 3,194,669 | 7/1965 | Koch | 116/217 |
| 3,518,961 | 7/1970 | Kovac | 116/217 |
| 4,064,828 | 12/1977 | Clark | 62/125 X |
| 4,187,799 | 2/1980 | Zwarun | 116/217 |

Primary Examiner—William E. Tapolcai
Attorney, Agent, or Firm—Staas & Halsey

[57] ABSTRACT

A foodstuffs thawing detector device (1) comprised of a water-filled container (2) in which detection or marker means (5, 8 or 10) is maintained in a stable position by the freezing of the water in the said container (2), where the said detection means will reach a position other than the said stable position when the water in the container melts. A preferred embodiment consists in a container (2) having an interior cavity defined by frusto-pyramidal formations (3) oriented in opposed directions and joined at their smaller bases in line with a central transverse plane (4); preferably, the said formations shall have a square base, and even a truncated arrangement (6) or the like, and detection means comprised of a ball member (5 or 8) having a high specific weight, maintained on the said central transverse plane (4) by the freezing of the water. In an alternative embodiment, the container is a simple pan (9) for the water (10), and the detection means is comprised of an amount of a water-soluble coloring substance (11) which will be poured into the pan once the water contained therein has frozen.

9 Claims, 3 Drawing Sheets

A-A

FROZEN FOODSTUFFS THAWING DETECTOR DEVICE

This invention relates to a device enabling a possible thawing of frozen foodstuffs to be detected any time, from the date of packaging to the date of consumption thereof.

As it is well known to experts in the foodstuffs freezing technique, it is absolutely necessary, in order to guarantee a suitable quality of the product, that the "cold chain" should not be interrupted, that is to say, that the foodstuff should not have been thawed at any time.

The only guarantees existing at present in this respect are those of the make or brand acquired, that of the distributor and that of the retailer, so that the customer can never be sure of the suitable quality of the acquired frozen product, even though such product has an appropriate frozen appearance at the time of purchasing it. Thus, for example, the possibility of the product having been thawed and subsequently frozen, due to accident during the manufacturing or the distributing chain, exists.

Additionally and assuming that the customer acquires a perfectly preserved product, no means exists for determining the correct preservation of the said product until its consumption date.

Thus, the object of the invention is to provide a device which enables a possible thawing of the frozen foodstuff to be unequivocally detected.

It is another object of the invention to provide a device of the aforesaid type whereby the condition of detection, that is to say, once the foodstuff has been thawed, becomes irreversible or at least hardly reproducible.

It is still another object of the invention to provide a device of the aforesaid type which is capable of carrying out manufacture at a low cost, so that it does not have a significant affect on the final price of the product.

According to the invention, these and other objects are accomplished since the device is comprised of a water-filled container in which detection means (markers) is maintained at a fixed stable position by the freezing of the liquid contained in the said container and since the said detection means will reach a position other than the said stable position when the said water melts, so that it is possible to unequivocally determine the correct preservation of the product from its date of manufacture to its date of consumption.

In a preferred embodiment of the invention, the container, made of transparent plastic material, forms internally a cavity defined by two frusto-pyramidal formations joined at their smaller bases, that is to say, they are oriented in opposed directions, in line with a central transverse joining plane, whilst the detection means is comprised of a ball or spherical member made of a material having a high specific weight, so that the said detection member or marker is maintained by the freezing of the liquid in the container on the said central transverse plane. In this manner, a thawing state will be detected by a displacement of the marker or the detection member will respect to the said central transverse plane.

As it can easily be understood, the marker ball, once the liquid in which it is immersed has melted, will necessarily take up a shifted position with respect to the said central transverse plane due to the equilibrium unstability of the said ball on the line joining the said frustopyramidal formations.

A yet preferred embodiment is that in which the frusto-pyramidal formations, the determinant of the interior cavity of the container, have a square base, that is to say, in such a manner that it defines a support for the marker ball having only four contact points (one for each side of the square).

Further preferred embodiments of the invention are those in which the interior cavity of the container is defined by truncated formations and the like.

According to another preferred embodiment of the invention, the detection means is comprised of a small amount of a water-soluble colouring substance, and the container is comprised of a simple water pan. In this manner, any thawing will be detected by a colouring of the water contained in the said container.

As will be understood by any person skilled in the art, to manufacture the device according to the embodiments described in the first place, the marker ball should necessarily be maintained in position on the central transverse plane of the container whilst the liquid contained therein is being frozen. This can be accomplished, for example, by means of a magnetic field or by two tailstock-like needles or shafts. The container may be closed by sealed covers or even by welding of determined weaker points on two of the opposed side faces.

Referring to the preparation of the detector device manufactured in accordance with the last described embodiment, the detection means, that is to say, the adequate portion or amount of water-soluble colouring substance, is inserted by means of suitable elements, once the water in the container has been frozen.

Other characteristics and advantages of the invention will become more apparent from the following description taken in conjunction with the drawings, relative to non-limiting modes of embodiment, in which:

FIG. 1 schematically shows a perspective view of a thawing detector device in accordance with the invention.

FIGS. 2 to 5 illustrate, respectively, a side elevational view, a front or rear elevational view, a plan view, and a cross-sectional view on the central plane of the device of FIG. 1.

FIG. 6 schematically shows another embodiment of the thawing detector device of the invention.

Figure 1:
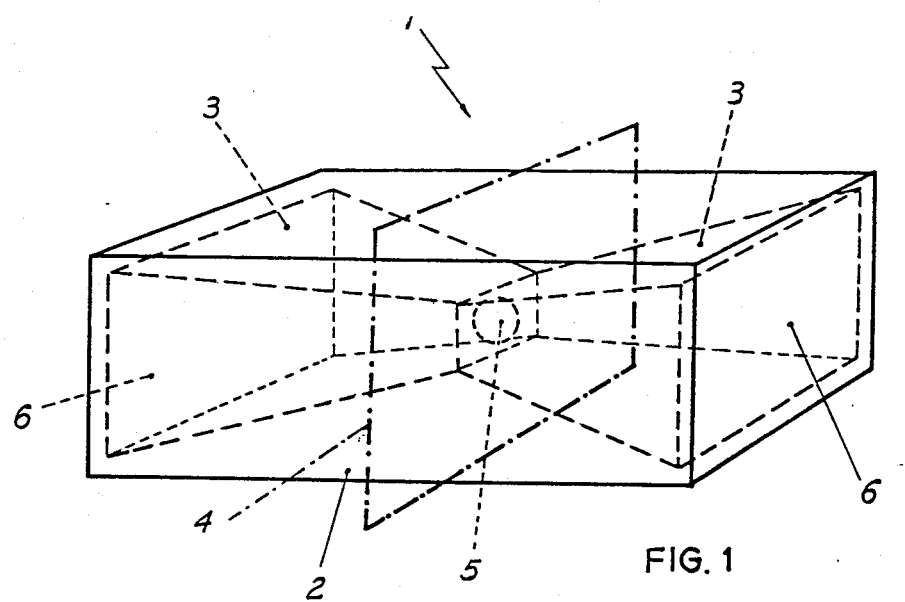
Figure 2:
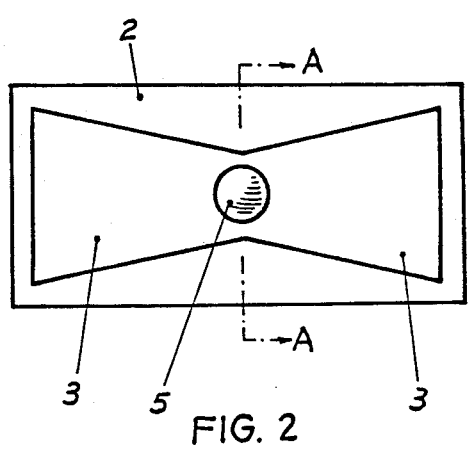
Figure 3:
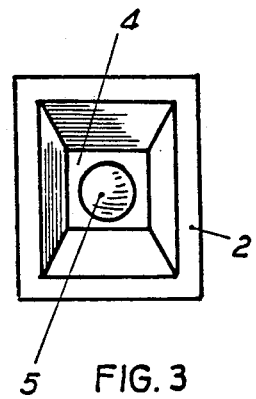
Figure 4:
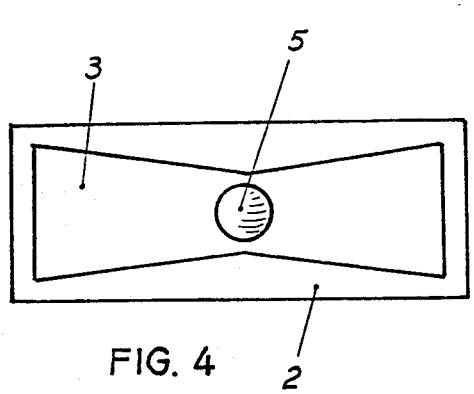

With reference to FIGS. 1 to 5, it can be seen that the detector device 1 is comprised of a parallelepiped container 2 having an interior cavity defined by frustopyramidal formations 3, oriented in opposed directions and joined at their smaller bases in line with a central transverse plane 4.

Still referring to FIGS. 1 to 5, on the plane 4, that is to say, on the interconnecting passage between the said frusto-pyramidal formations 3, is placed a ball 5 serving as the marker member or detection means.

Figure 5:
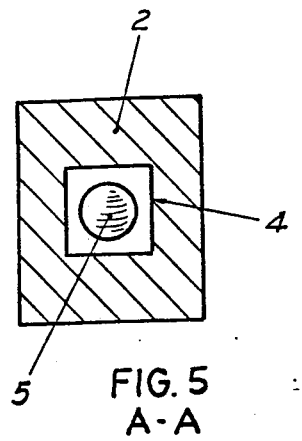

As can be seen in more detail in FIG. 5, the marker ball 5 only rests on four points, one for each side, of the central transverse plane 4, so that the equilibrium of the said ball is completely unstable. Therefore if the water contained in the container melts, the said ball will unfailingly take up a position other than the said central position.

Naturally, to manufacture the device 1, the marker ball 5 should necessarily be maintained at the central position 4 whilst the water in the container is being frozen. This can be accomplished, for example, by magnetic field or by pins or needles (not represented) which center like a tailstock, the ball 5 with respect to the central transverse plane 4.

Figure 6:
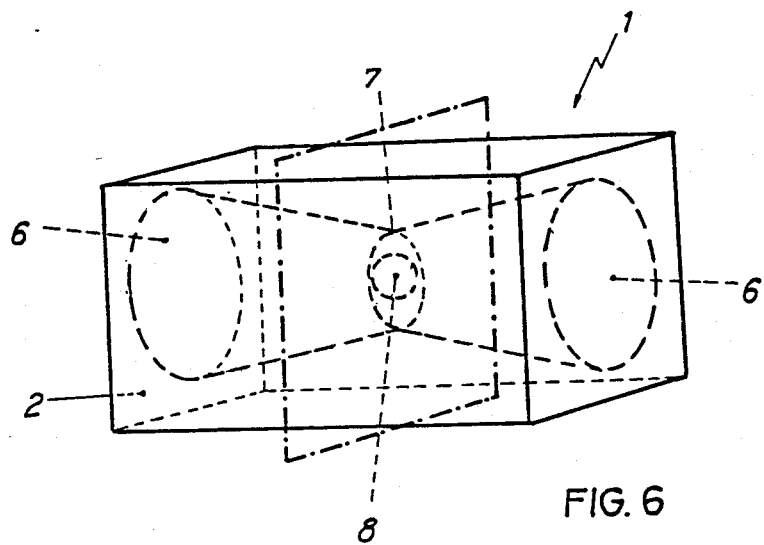

In the alternative embodiment of the detector device illustrated in FIG. 6, the interior of the container 2 is defined by a cavity determined by frustoconical formations 6, joined at their smaller bases in line with a central transverse plane 7, so that a marker ball 8 is similarly arranged on the said central transverse plane 7.

Figure 7:
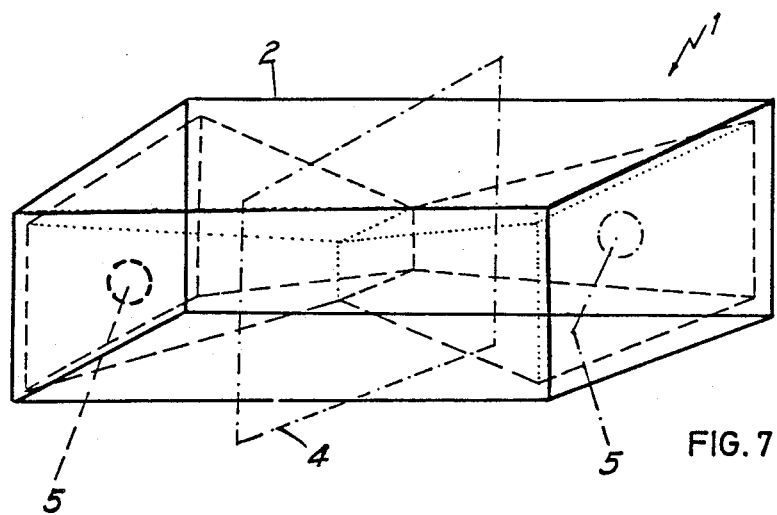
FIG. 7 shows a condition of detection in the device of FIG. 1.

As it will easily be understood with reference to FIGS. 1 and 7, when the marker ball 5 or 8 is maintained at the central position of the plane 4 or 7 by the freezing of the liquid in the container 2, a thawing condition will, unfailingly, be indicated by a separation of the marker ball 5 from the central transverse plane 4 or 7, due to the unstable equilibrium of the said ball 5 or 8 with the melted water. Thus, even though the device (and therefore the product) were to be subsequently frozen, the said marker ball 5 or 8 will never return to the original central position, unless a complex centering process is carried out which would be extremely costly and consequently commercially unprofitable.

Figure 8:
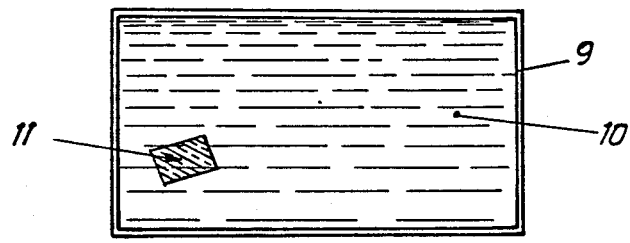
FIG. 8 shows another alternative embodiment of the detector device of the invention.
Figure 9:
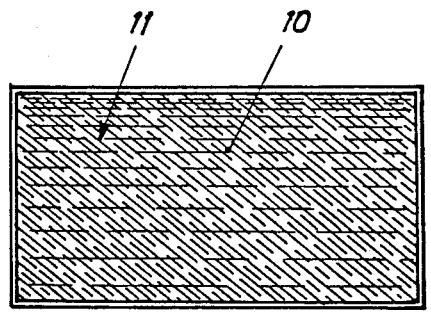
FIG. 9 shows the condition of detection of a thawing in the device of FIG. 8.

Referring now to FIG. 8, the detector device 1 is comprised of a simple pan 9 for the water 10, and an amount of a water-soluble colouring substance 11 will be inserted by means of the suitable technique, once the water has frozen. In this manner, if the water were to melt it would dissolve the portion of colouring substance 11, so that a subsequent freezing of the water in the device would always be detected by a certain colouring of the water contained therein.

Further mention can be made to the former embodiments in which covers or access zones to the interior of the container must be provided to enable the fastening of the marker ball or the insertion of a portion of colouring substance, which will be carried out in a suitable manner in order to prevent any possibility of handling subsequent to manufacture.

Additionally, the outer part of the container 2 could be provided with elements to be fixed or fastened to the frozen product packet, not represented, in the form of a guarantee seal so that a device which has detected a thawing condition cannot be substituted by a new device.

I claim:

1. Frozen foodstuffs thawing detector device comprising:
   a container having sides for holding a liquid;
   detection or marker means maintained at a position due to the freezing of the liquid said detection or marker means moving to another position along one of the sides when the liquid melts, and comprising a material having a high specific weight and being capable of being magnetized.

2. A thawing detector device comprising:
   a container for holding a liquid and having sides defining an interior cavity shaped as two frusto-pyramidal formations oriented in opposed directions and joined at their smaller bases in line with a central transverse plane; and
   detection or marker means maintained on the central transverse plane by the freezing of the liquid contained in said container.

3. Device according to claim 2, characterised in that the container will present an inner configuration defined by two truncated formations oriented in opposed directions and joined at their smaller bases in lane with a central transverse plane.

4. Device according to claim 2, characterised in that said detection or marker means comprises a spherical member or marker ball will be made comprising a material having a high specific weight.

5. Device according to claim 2, characterised in that said detection or marker means comprises a spherical member or marker ball will be made comprising a metallic material capable of being magnetised.

6. Frozen foodstuffs thawing detector device comprising:
   a container having sides for holding a liquid and having an inner configuration defined by two truncated formations oriented in opposed directions and joined at their smaller bases in line with a central transverse plane; and
   detection or marker means maintained at a position due to the freezing of the liquid said detection or marker means moving to another position along one of the sides when the liquid melts.

7. Device according to claim 6, characterised in that said detection or marker means comprises a spherical member or marker ball will be made comprising a material having a high specific weight.

8. Device according to claim 6, characterised in that said detection or marker means comprises a spherical member or marker ball will be made comprising a metallic material capable of being magnetised.

9. Frozen foodstuffs thawing detector device comprising:
   a container having sides for holding a liquid;
   detection or marker means maintained at a position due to the freezing of the liquid said detection or marker means moving to another position along one of the sides when the liquid melts, and comprising a material having a high specific weight and being capable of being magnetized, and comprising a metallic material capable of being magnetized.

* * * * *